United States Patent [19]

Kauppinen et al.

[11] Patent Number: 5,313,406

[45] Date of Patent: May 17, 1994

[54] PROCEDURES FOR ANALYZING MULTICOMPONENT FT-IR SPECTRA FOR UNKNOWN MIXTURES OF GASES

[75] Inventors: Jyrki Kauppinen; Pekka Saarinen, both of Helsinki, Finland

[73] Assignee: Temet Instruments Oy, Helsinki, Finland

[21] Appl. No.: 896,689

[22] Filed: Jun. 10, 1992

[51] Int. Cl.$^5$ .............................................. G06F 15/20
[52] U.S. Cl. .................................... 364/498; 364/502; 250/341
[58] Field of Search ............... 364/498, 497, 499, 500, 364/502; 250/343, 341, 338.1, 338.2, 339, 390.07

[56] References Cited

U.S. PATENT DOCUMENTS

| | | | |
|---|---|---|---|
| 4,008,388 | 2/1977 | McLaffery et al. | 364/498 |
| 4,365,303 | 12/1982 | Hannah et al. | |
| 4,514,635 | 4/1985 | Ishida et al. | 250/343 |
| 4,652,755 | 3/1987 | Solomon et al. | 250/341 |
| 5,121,337 | 6/1992 | Brown | 364/498 |

Primary Examiner—Thomas G. Black
Assistant Examiner—Tan Q. Nguyen
Attorney, Agent, or Firm—Merchant, Gould, Smith, Edell, Welter & Schmidt

[57] ABSTRACT

Procedures are provided for analyzing multicomponent FT-IR spectra for unknown mixtures of gases. In the analysis, the FT-IR spectrum is measured for the particular unknown mixture of gases to be analyzed. The operations of the multicomponent analysis are divided into three different levels so that the most laborious operations, which have to be performed very seldom or only once, are on the highest level. Rapid calculation operations to be performed in connection with each spectrum analysis are on the lowest level. The levels are as follows: 1) Forming a spectrum library; 2) Introducing a new basis and adding a new vector to the old basis; and 3) Individual analysis. Variances, error limits, and residual spectra are calculated in the analysis. A windowing procedure is followed to reject spectrum portions where the transmittance approaches zero or which do not contain real information for some other reason. Determination of the partial pressures is speeded up by storing predetermined calculation results in a data file for later usage, thereby avoiding unnecessary recalculation of certain equations utilized in the analysis.

5 Claims, 3 Drawing Sheets

FIG. 2
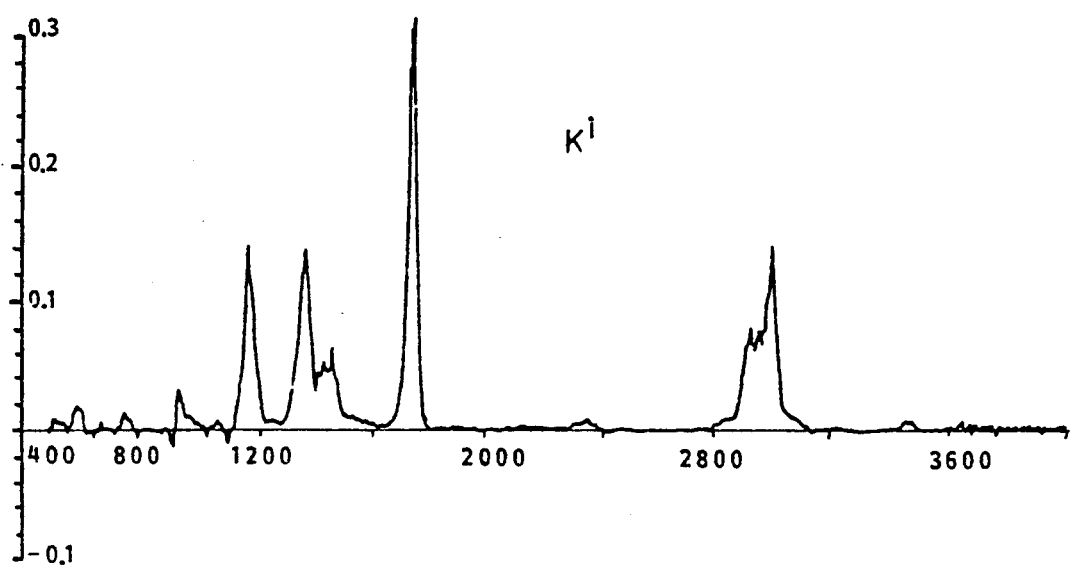
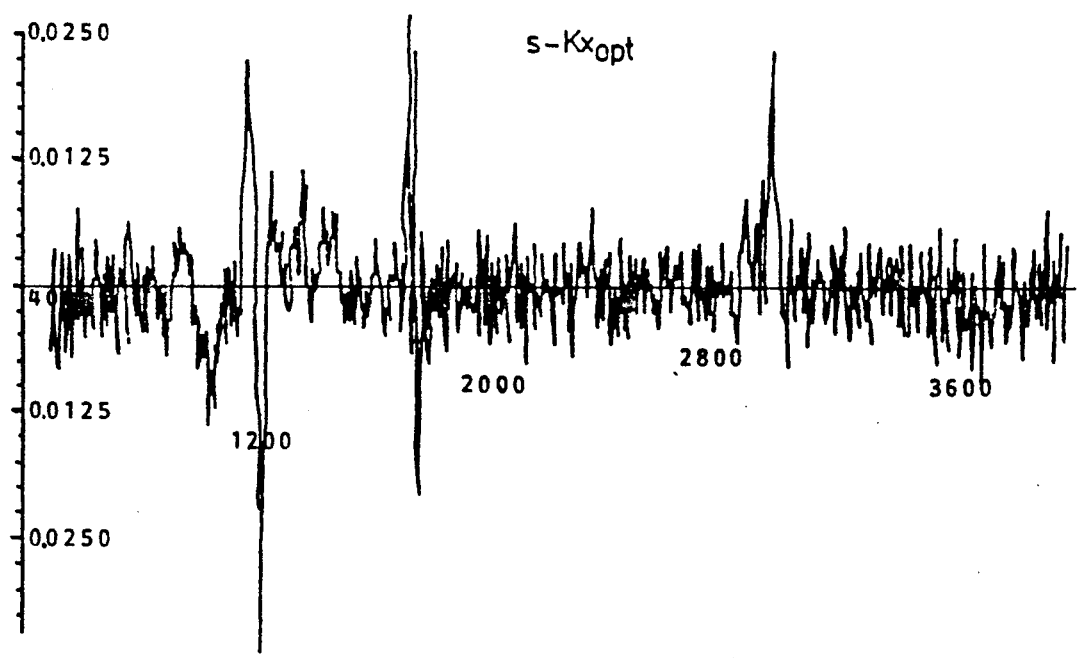

PROCEDURES FOR ANALYZING MULTICOMPONENT FT-IR SPECTRA FOR UNKNOWN MIXTURES OF GASES

BACKGROUND OF THE INVENTION

The present invention concerns the procedure for analyzing a FT-IR-spectrum of an unknown mixture of gases, about which we do not know the constituent gases, not to mention their partial pressures. Instead we know a large set of library spectra of pure molecular gases, measured in known pressures and with the same interferometer as the unknown sample.

1. Field of the Invention

In FT-IR-spectroscopy in multicomponent analysis we have the IR-spectrum of an unknonw mixture of gases, about which we co not inow the constituent gases, not to mention their partial pressures. Instead we know a large set f library spectra of pure molecular gases, measured in known pressures and wih the same interferometer as the unknown sample. By using these pure spectra we ought to calculate the patial pressures of the pure gases in the mixture, with error limits. The errors in the obtained values arise from the measurement noise in the spcectra. Because the calculation of such partial pressures that best explain the mixture spectrum is a relatively simple task, we shall consider it only briefly and concentrate on the calculation of their error limits. We chall also consider the optimal choice of the resolution providing as small error limits as possible and the application of the non-negativity constraint for the partial pressures. In addition to gas spectra, all the calculations apply to spectra of non-interacting liquids as well.

2. Description of the Prior Art

Let us denote by s the measured mixture spectrum to be analyzed and let $\{K^j|j=1, \ldots ,m\}$ be the set of library spectra with which we are trying to explain s. We assume that all the spectra are linearized, i.e. that on the y-axis there is always the negative logarithm of the transmittance (except possible some constant coefficient). This means that we are using the absorbance scale. Then, according to Beer's law, s is some linear combination of the spectra $K^j$, or $$s = \sum_{j=1}^{M} x_j K^j. \tag{1}$$

Our task is to determine such coefficients $x_j$ by which s is explained as well as possible. After that the partial pressures of the pure gases in the mixture ar obtained by multiplying the measuring pressures of the corresponding library spectra by their coefficients in the linear combination.

Because all the spectra are only known at equally spaced tabelling points $v_1, \ldots ,v_n$, s and $k^j$ can be treeated as vectors, and we can state Eq. 1 in vector form as $$x_1 \begin{pmatrix} K_{11} \\ K_{21} \\ \cdot \\ \cdot \\ \cdot \\ K_{N1} \end{pmatrix} + x_2 \begin{pmatrix} K_{12} \\ K_{22} \\ \cdot \\ \cdot \\ \cdot \\ K_{N2} \end{pmatrix} + \ldots + x_M \begin{pmatrix} K_{1M} \\ K_{2M} \\ \cdot \\ \cdot \\ \cdot \\ K_{NM} \end{pmatrix} = \begin{pmatrix} s_1 \\ s_2 \\ \cdot \\ \cdot \\ \cdot \\ s_N \end{pmatrix} \tag{2}$$

This equation can be further simplified by collecting all $K^j$-vectors together into a matrix K, which gives us the matrix equation $$Kx=s, \tag{3}$$

where $$K = \begin{pmatrix} K_{11} & K_{12} & \ldots & K_{1M} \\ K_{21} & K_{22} & \ldots & K_{2M} \\ \cdot & \cdot & & \cdot \\ \cdot & \cdot & & \cdot \\ \cdot & \cdot & & \cdot \\ K_{N1} & K_{N2} & \ldots & K_{NM} \end{pmatrix}$$

and x is the coefficient (column) vector containing the coefficients $x_j$ of the pure spectra.

SUMMARY OF THE INVENTION

Now all the spectra that can be exactly explained by the used set of M pure spectra are expressible in the form Kx. However, even if the set $\{K^j|j=1, \ldots ,M\}$ included all the components in the mixture, there always exists some noise in the spectra so that s never lies exactly in the vector space generated by the vectors $K^j$. Thus we have to content ourselves with such a linear combination Kx of the pure spectra that is as near as possible to the vector s. This means that we have to minimize the norm of the residual vector s-Kx, which remains unexpalined. Thus we can write our problem in the form of an optimization problem as $$\|s-Kx\| = \min! \tag{4}$$

The optimization parameters are then the comonents of the coefficient vector x.

The optimal value of the coefficient vector depends on which vector norm we are using. Let us now define this norm from the condition $$\|v\| = \sqrt{\frac{1}{N} \sum_{i=1}^{N} v_i^2}. \tag{5}$$

This is the usual square sum fector norm except for the constant coefficient $1/N$. The purpose of this coefficient is to make vector norm as independent as possible of the number of the data N (and thus on the resolution). It has no effieit on the solutio of the optimization problem 4. The solution of problem 4 is now obtained by setting the gradient of the residual vector equal to zero or $$\nabla|s-Ks|=0 \tag{6}$$

a very simple calculation shows that this condition is fulfilled by the coefficient vector $$x_{opt}=(K^TK)^{-1}K^Ts \tag{7}$$

(provided, of course, that $N \geq M$.) This is nknown in literature as the pseudoinverse solution of the matrix equation Kx=s (see e.g. [1]). Because of the choice—see Eq. 5—of the norm, this can also be called the least square solution. The matrix $K^TK$ is invertible, if and only if the vectors $K^j$ are linearly independent. If they are not, the best solution is not unique. If the error limits are not meeded, we suggest the procedure described below for the application of Eq. 7.

We now define theinner produce $<a|b>$ of two vectors a dn b from $$(a/b) = \frac{1}{N} \sum_{i=1}^{N} a_i b_i. \tag{8}$$

The coefficient 1/N again ensures that the inner product is as independent as possible of the number of the data. Likewise the usual relationship $\|v\| = <v|v>^{\frac{1}{2}}$ between norm and inner product holds true. Now we see that equation 7 can be written in the form $$X_{opt} = A^{-1} y \tag{9}$$

where $$A_{ij} = <K^i|K^j> \tag{10}$$

and $$Y_j = <K^j|s>. \tag{11}$$

Thus the matrix A contains the inner products of the used lirary specra with each other and may be called the inner product matrix. If we are not interested in the error limits of the coefficients, we can calculate beforehand all possible inner products into a library. Then, in a particular analysis, we need only pick out those inner products corresponding to teh set of library spectra to be used in this analysis to build up the matrix A, calculate the vector y and solve the matrix equation $Ax=y$. If this is done by using the Gauss elimination method (see e.q. '2, p. 179]), there is no need to invert A, and the analysis is a very rapid procedure.

All noise in the spectra generate errors in the optimal coefficient vector of Eq. 9. In this work we shall only deal with the noise in the mixture spectrum s. The noise in the library spectra $K^j$ could approximately be taken into account, too, but we shall omit it here for two reasons. For the first the treatise would be too long and only approximate. For the second, in practical applications it is sensible to register the libray spectra with much higher accuracy (i.e. by co-adding a much larger amount of individual runs) than the mixture spectrum, which is obtained with a rapid measurement. Thus, practically seen, all the noise is in the mixture spectra and the library spectra can be considered as noiseless.

Above we have been using the library spectra $K^j$ as the basis vectors, with which all measurements were explained in the form $$\sum_{j=1}^{M} x_j K^j$$

or Kx. However, when calculating the error limits, it is advantageous to use an orthogonal basis, which generates the same vector space as the original library spectra. We construct these orthogonal basis vectors by the Gram-Schmidt orthogonalization method (see some textbook of linear algebra, e.g. [2, p. 138]). This means that the new basis vectors $\{K'^j\}$ are defined by the recursive group of equations $$\begin{cases} K'^1 = K^1 \\ K'^2 = K^2 - \frac{(K^2|K'^1)}{\|K'^1\|^2} \\ \cdot \\ \cdot \\ K'^j = K^j - \sum_{x=1}^{j-1} \frac{<K^j|K'^x>}{\|K'^x\|^2} \\ \cdot \\ \cdot \end{cases} \tag{12}$$

Thus the old basis vectors are obtained from the new ones by $$\begin{cases} K^1 = K'^1 \\ K^2 = \frac{(K^2|K'^1)}{\|K'^1\|^2} K'^1 + K'^2 \\ \cdot \\ \cdot \\ K^j = \sum_{x=1}^{j-1} \frac{<K^j|K'^x>}{\|K'^x\|^2} K'^x + K'^j \\ \cdot \\ \cdot \end{cases} \tag{13}$$

Next we define a transformation matrix Q as $$Q_{ij} = \begin{cases} 0, & i > j \\ 1, & i = j \\ \frac{<K^j|K'^i>}{\|K'^i\|^2} & j > i. \end{cases} \tag{14}$$

(Thus Q is an upper triangular matrix.) Now the transformation of the basis can be expressed very compactly as $$K = K'Q. \tag{15}$$

The transformation of coefficient vectors between these two bases is governed by the equation $$X = Q^{-1} X' \tag{16}$$

Thus we shall need the inverse of Q. After some tedious calculations we discover that it is an upper triangular matrix given by $$Q_{ij}^{-1} = \begin{cases} 0, & i > j \\ 1, & i = j \\ -\sum_{l=i+1}^{j} Q_{il} Q_{lj}^{-1} & j > i \end{cases} \tag{17}$$

The elements with $j>i$ have to be calculated in the order $i=M-1, \ldots, 1$.

The determination of the best coefficient vector is very simple in the basis K'. Because this basis is orthogonal, $<K'^i|K'^j> = \delta_{ij}$ and the inner product matrix A' (see (Eq. 10)) is diagonal, $$A' = \text{diag}(\|K'^1\|^2, \|K'^2\|^2, \ldots, \|K'^M\|^2). \quad (18)$$

Thus the best coefficient vector $x'_{opt}$ is given by (see Eq. 9)

$$x_{opt}' = A'^{-1} y' = (K'^T K')^{-1} K'^T s = \qquad (19)$$

$$\begin{pmatrix} \|K'^I\|^{-2} & & 0 \\ & \cdot & \\ & & \cdot \\ 0 & & \|K'^M\|^{-2} \end{pmatrix} \frac{1}{N} K'^T s$$

or $$x_{opt,j}' = \frac{<K'^j|s>}{\|K'^j\|^2}$$

Vector $X'_{opt}$ gives the optimal coefficients of the orthogonal basis vectors $K'^j$. The corresponding coefficient vector x of the real pure spectra $K^j$ is then $Q^{-1} X'_{opt}$. As is intuitively very clear, this equals the optimal coefficient vector $X_{opt}$ in the original basis. This fact can also be proved formally as follows:

$$x'_{opt} = (K'^T K')^{-1} K'^T s = [(Q^{-1})^T K^T K Q^{-1}]^{-1}$$
$$(Q^{-1})^T K^T s = Q (K^T K)^{-1} Q^T (Q^T)^{-1} K^T s =$$
$$Q(K^T K)^{-1} K^T s = Q x_{opt}.$$

This means that $$X_{opt} = Q^{-1} x'_{opt}. \quad (21)$$

Next we consider the effect of measurement noise on the optimal coefficient vector of Eq. 9 or 21. For this purpose we divide s into two separate parts as $$S = S^o + S^e \quad (22)$$

where $s^o$ is the correct noiseless mixture spectrum and $s^e$ includes the noise. Because the dependence between s and $x_{opt}$ is linear, the coefficient vector $x_{opt}$ can also be divided into the correct coefficient vector $X_{opt}^o$ and the error vector $x_{opt}^e$, which obey $$X_{opt}^o = (K^T K)^{-1} K^T s^o = Q^{-1} (K'^T K')^{-1} K'^T s^o \quad (23a)$$

and $$s_{opt}^e = (K^T K)^{-1} K^T s^e = Q^{-1} (K'^T K')^{-1} K'^T s^e \quad (24a)$$

or equivalently $$x_{opt}^0 = A^{-1} y^0 = Q^{-1} A'^{-1} y'^0 \quad (23b)$$

and $$x_{opt}^e = A^{-1} y^e = Q^{-1} A'^{-1} y'^e \quad (24b)$$

Thus the errors of the coefficients depend linearly on the measurements. The components of the noise vector $s^e$ are normally distributed with zero mean. Even if the noise data of an individual measurement were not normally distributed for some reason or other, according to the central limit theorem of the probability calculus the sum of several noise data is always normally distributed, and in practice we alsways co-add several individual runs to obtain one spectrum. Thus, if we designate their standard deviation by $\sigma_s$, we can write $$s_1^e \div N(0, \sigma_s^2). \quad (25)$$

(This expression tells that $s_1^e$ obeys the normal distribution with a mean 0 and a variance $\sigma_s^2$. Note that N stands for the normal distribution, while N is the number of the data.) Because we know the distribution of the nosie data, we can now calculate the distributions of the errors of the coefficients by using Eq. 24. This is what we are going to do next.

First we state without proof a well-known result of the probability calculus concerning the normal distribution.

Let $z_i \div N(\mu_{1,1}^2)$ be independent and $a_1 g R$. Then $$\sum_i a_i z_i \div N\left(\sum_i a_i \mu_i, \sum_i a_i^2 \sigma_i^2\right). \quad (26)$$

This means that a linear combination of independent normally distributed random variables is normally distributed, too. By using this result we get for the components of the vector $y'^e$, which appears in the expression for $x_{opt}^e$ in Eq. 24b:

$$y'^e_j = \frac{1}{N} (K'^j)^T s^e \div N\left(0, \frac{1}{N^2} \sum_{l=1}^{N} (K'^j_l)^2 \sigma_s^2\right) = \quad (27)$$

$$N\left(0, \frac{\sigma_s^2}{N} \|K'^j\|^2\right)$$

Now we need another result of the probability calculus, stating that two normally distributed random variables $z_1$ and $z_2$ are independent if and only if the correlation between them is zero. The correlation is defined by $$e(z_1, z_2) = \frac{\text{cov}(z_1, z_2)}{\sqrt{\text{Var}(z_1)} \sqrt{\text{Var}(z_2)}},$$

where $$\text{cov}(z_1, z_2) = E[(z_1 - E(z_1))(z_2 - E(z_2))]$$

and E is the expectation operator. Because the expectation values $E(y'^e_j)$ are zeroes, two components $y'^e_j$ and $y'^e_k$ are independent random variables if and only if $E(y'^e_j y'^e_k)$ is zero.

$$E(y'^e_j y'^e_i) = \frac{1}{N^2} E[(K'^j s^e)(K'^k s^e)] =$$

$$\frac{1}{N^2} E\left[\sum_{i,l} K'^j_i K'^k_l E(s^e_i s^e_l)\right] = \frac{1}{N} E[(s^e)^2](K'^j | K'^k),$$

for $E(s_1^e s_1^e) = \delta_{11} E[(s_1^e)^2]$ and all the random variables $s_1^e$ are identically distributed. The independence of $y'^e_j$ and $y'^e_k$ now follows from the fact that the basis K' is orthogonal. It further follows from Eqs. 19, 26 and 27 that $$x_{opt,j}^{\prime\epsilon} \div N\left(0, \frac{1}{N} \frac{1}{N\|K^j\|^2} \sigma_s^2\right) \tag{28}$$

and that the components of $s'_{opt}{}^3$ are independent. Thus we may once more use result 26 to obtain $$x_{opt,j}^{\epsilon} = (Q^{-1}x'_{opt})_j \div N\left(0, \frac{\sigma_s^2}{N} \sum_{l=1}^{M} \frac{(Q_{jl}^{-1})^2}{\|K^l\|^2}\right). \tag{29}$$

If we use the non-orthogonal basis K, the left-hand equality of Eq. 24 gives $$x_{opt,j}^{\epsilon} \div N\left(0, \sigma_s^2 \sum_{l=1}^{M} P_{jl}^2\right), \tag{30}$$

where P is the pseudoinverse matrix $$P = (K^T K)^{-1} K^T = \frac{1}{N} A^{-1} K^T. \tag{31}$$

Now that we know the distributions of the errors of the coefficients, we are also able to give error limits for the coefficients. Because these errors are normally distributed random variables, we cannot give any upper limits for them. Instead we can calculate such error limits for the correct coefficients to fall with a given probability within them. Let us now assume that we want such an error limit $v_j$, that the coefficient $x_{opt,j}$ belongs with a probability p in the interval $[x_{opt,j}{}^0 - v_j, s_{opt,j}{}^0 v_j]$. This means that $$P(x_{opt,j}^{\epsilon}\epsilon[-v_j, v_j]) = p.$$

If we denote $\Phi$ the distribution (N(0,1)), we get $$p = P\left(\frac{x_{opt,j}^{\epsilon}}{\sqrt{Var(x_{opt,j}^{\epsilon})}} \epsilon \left[\frac{-v_j}{\sqrt{Var(x_{opt,j}^{\epsilon})}}, \frac{v_j}{\sqrt{Var(x_{opt,j}^{\epsilon})}}\right]\right)$$

$$= \Phi\left(\frac{v_j}{\sqrt{Var(x_{opt,j}^{\epsilon})}}\right) - \Phi\left(\frac{-v_j}{\sqrt{Var(x_{opt,j}^{\epsilon})}}\right) =$$

$$2\Phi\left(\frac{v_j}{\sqrt{Var(x_{opt,j}^{\epsilon})}}\right) - 1,$$

from which $$\Phi\left(\frac{v_j}{\sqrt{Var(x_{opt,j}^{\epsilon})}}\right) = \frac{1+p}{2} \tag{32}$$

or $$v_j = \sqrt{Var(x_{opt,j}^{\epsilon})} \; \Phi^{-1}\left(\frac{1+p}{2}\right).$$

For example, the 50% error limit for the coefficient of library spectrum number j is given by the expression $$\sqrt{Var(x_{opt,j}^{\epsilon})} \; \Phi^{-1}\left(\frac{1+0.5}{2}\right) \approx 0.674490 \sqrt{Var(x_{opt,j}^{\epsilon})}.$$

The variance of $x_{opt,j}^{\epsilon}$ is obtained from result 29 or 30 as $$Var(x_{opt,j}^{\epsilon}) = \frac{\sigma_s^2}{N} \sum_{l=1}^{M} \frac{(Q_{jl}^{-1})^2}{\|K^l\|^2} = \sigma_s^2 \sum_{l=1}^{M} P_{jl}^2. \tag{33}$$

It might first appear that the original basis K would be the most sensible choice to be used in the analysis, because the coefficients and their variances are then obtained from the very simple results 9 and 30. However, every time we add a new library spectrum into the analysis, the inner product matrix A is changed, and we have to re-calculate its inverse, which is needed at least in Eq. 31, and in inverting a general matrix we do not have a simple formula like Eq. 17. In addition we have to re-calculate the matrix product $A^{-1}K^T$ to obtain P. The previous value of $x_{opt}$ also becomes useless. When using the orthogonal basis K', the coefficients and their variances are given by Eqs. 20, 21 and 29. Let us now have a closer look at what happens when we have to add a new library spectrum to the set of the library spectra used in the analysis and the basis K' is in use.

First of all we must calculate a new orthogonal spectrum $K'^{M+1}$ from group of equations 12. While we calculate the coefficients appearing in the expression $K'^{M+1}$ in group of equations 12, we also obtain the elements of the column M+1, which must be added to the transformation matrix Q. (The new row elements $Q_{M+1,j}$, j22 M+1 are zeroes according to Eq. 14.) This new column means that the inverse transformation matrix $Q^{-1}$ is changed, too. However, we see from Eq. 17 that an arbitrary element of $Q^{-1}$ depends only on the previously calculated elements of $Q^{-1}$ in the same column and on the elements of Q in the same and previous columns. Thus the previous elements of $Q^{-1}$ are not changed and we need only calculate M new elements $Q_{M,M+1}^{-1}, \ldots, Q_{1,M+1}^{-1}$ which are given by Eq. 17 as $$Q_{i,M+1}^{-1} = -\sum_{l=i+1}^{M+1} Q_{il} Q_{l,M+1}^{-1}. \tag{34}$$

(Because $Q^{-1}$ is an upper triangular matrix, all the elements on the new row $Q_{M+1}^{-1}$ are either zero or one.)

If we are still analyzing the same measurement s as before updating $Q^{-1}$, the following corrections remain to be made to the previous calculations:

1) We have to add a new component $x'_{opt,M+1}$ into the vector $x'_{opt}$. It is obtained from Eq. 20.
2) According to Eq. 21, $x_{opt,M+1} = Q_{M+1}^{-1} x'_{opt} = x'_{opt,M+1}$. To the other components $x_{opt,j}$ we must add the term $Q_{j,M+1}^{-1} x'_{opt,M+1}$.

3) According to Eq. 29 $\text{Var}(s_{opt,M+1}^e) = \sigma_x^2/(N\|K'^{M+1}\|^2)$. To the other variances $\text{Var}(x_{opt,j}) = \text{Var}(x_{opt,j}^e)$ we must add the term $$\frac{\sigma_s^2(Q_{j,M+1}^{-1})^2}{N\|K'^{M+1}\|^2}.$$

Because the squares of norms $\|K'^j\|^2$ are needed repeatedly, it is sensible to store them in a vector, after they have been calculated in group of equations 12. The use of double precision real numbers is highly recommendable in computer programs.

BRIEF DESCRIPTION OF THE DRAWINGS

The invention is described in the following detailed in the aid of examples, referring to the drawings attached wherein

FIG. 2 discloses an illustration of what happens when the used library is deficient; the same mixture spectrum has been analyzed as in FIG. 1, but now the spectrum of 2-butanone has been removed fro mthe used set of library spectra;

(a) $\dfrac{\partial\|d\|^2}{\partial x_j} = 0$ and $x_j \geq 0$ or (b) $\dfrac{\partial\|d\|^2}{\partial x_j} > 0$ and $x_j = 0$.

DESCRIPTION OF THE PREFERRED EMBODIMENT

Figure 1:
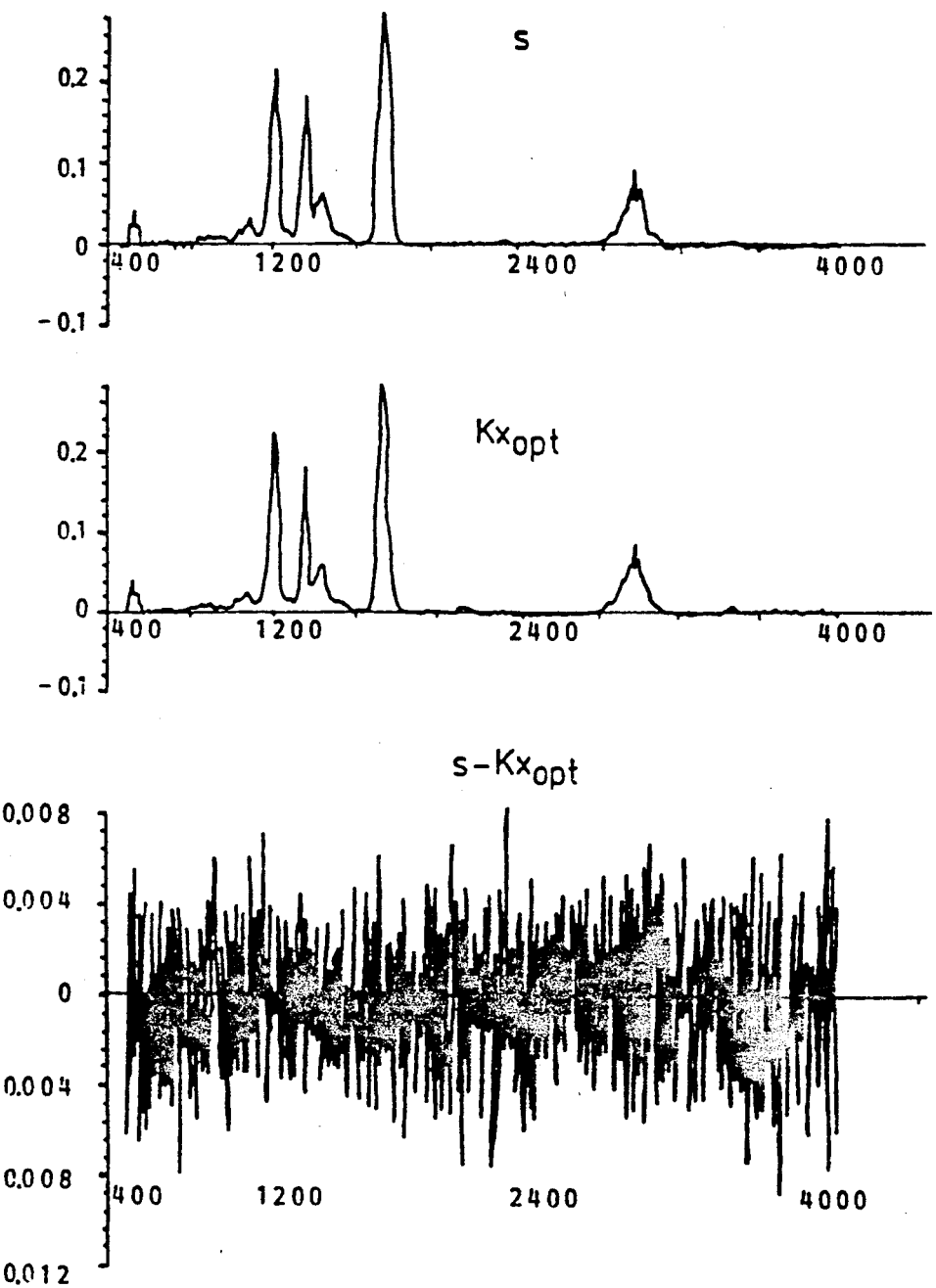
FIG. 1 is a mixture spectrum s, the linear combination $Kx_{opt}$ of the library spectra that best explains s and the residual spectrum $S - Kx_{opt}$, which then remains unexplained (appears magnified in the figure)

In this chapter we shall demonstrate the method by analyzing the spectrum of a simple mixture of gases. The coefficients are calculated by using Eqs. 20 and 21 and their error limits by Eqs. 29 and 32. We shall use 50% error limits here, because they give a very good idea of the orders of magnitude of the errors. In FIG. 1 we see the mixture spectrum s to be analyzed by using a set of 12 library spectra. In the table 1 we see the components of $x_{opt}$ with error limits. The three first components are the background spectra. These are all the spectra or functions, which are present also in the background measurement or which can arise from an error data in the interferogram. They can have negative coefficients as well as positive. The mixture spectrum s and the library spectra $K^j$ are measured with identical arrangements, but extra artificial noise has been added to s in order to simulate poorer accuracy, which is assumed in this work. In addition we see the linear combination $Kx_{opt}$ of these library spectra that best explains s. Also shown is the remainder spectrum $s - Kx_{opt}$, which then remains unexplained. As we may see, the remainder spectrum consists of pure white noise. This indicates that the analysis has been successful and that the 12 library spectra used suffice to explain the measurement. In the table 1 we can see the result of the analysis or the optimal coefficient vector $x_{opt}$.

The optimal coefficient vector

| | Basis function | Co-efficient | Error limit (50%) |
|---|---|---|---|
| background | No. 1: Constant function (1) | 0.0001 | 0.0001 |
| | No. 2: Water | −0.0062 | 0.0029 |
| | No. 3: Carbon dioxide | −0.0002 | 0.0037 |
| | No. 4: Methanol | −0.0013 | 0.0027 |
| | No. 5: Ethanol | 0.0724 | 0.0023 |
| | No. 6: 2-Butanone | 0.2193 | 0.0017 |
| | No. 7: Chloroform | −0.0011 | 0.0005 |
| | No. 8: Acetone | 1.2805 | 0.0028 |
| | No. 9: Toluene | 0.0014 | 0.0015 |
| | No. 10: Methyl acetate | 0.0006 | 0.0004 |
| | No. 11: Methyl formate | 0.0035 | 0.0008 |
| | No. 12: Methyl propanoate | 0.1351 | 0.0007 |

The partial pressure of the library gas number j is not obtained by multiplying its measuring pressure by its coefficient $x_{opt,j}$. These components, which do not exist in the mixture, have small positive or negative coefficients with the same order of magnitude as their error limits. If we add some background spectra to the analysis, the optimal removal of the background of the spectrum is also performed automatically. In fact, the three first spectra (water, carbon dioxide and the constant function, which has the value of one everywhere) in the table are background spectra. Because we are not interested in their exact coefficients, but merely want to get rid of them, they need not even be pure, but can contain each other. The library spectra may contain some carbon dioxide and water, too, with no effect on the values of their coefficients. The only effect is that the coefficients and error limits of the background spectra are not reliable. The coefficients of the background spectra can have negative values as well as positive. It can actually happen, for instance, that there is more carbon dioxide present during the measurement of the background interferogram than there was during the measurement of the sample interferogram.

In FIG. 2 we see what happens if the set of library spectra used is not sufficient for explaining the compound spectrum, in the table 2 we can see the results of the analysis or the optimal coefficient vector $x_{opt}$.

The optimal coefficient vector

| Basis function | | Coefficient | Error limit (50%) |
|---|---|---|---|
| No. 1: | Constant function (1) | −0.0001 | 0.0001 |
| No. 2: | Water | 0.0249 | 0.0029 |
| No. 3: | Carbon dioxide | −0.0197 | 0.0037 |
| No. 4: | Methanol | 0.0446 | 0.0027 |
| No. 5: | Ethanol | 0.1184 | 0.0022 |
| No. 6: | 2-Butanone | — | — |
| No. 7: | Chloroform | −0.0053 | 0.0005 |
| No. 8: | Acetone | 1.5193 | 0.0021 |
| No. 9: | Toluene | 0.0112 | 0.0015 |
| No. 10: | Methyl acetate | −0.0098 | 0.0004 |
| No. 11: | Methyl formate | 0.0512 | 0.0007 |
| No. 12: | Methyl propanoate | 0.1111 | 0.0007 |

The same mixture spectrum is used as in FIG. 1, but the spectrum of 2-butanon, which is an important constituent of the mixture, is not included in the analysis. Now the minimized residual spectrum is not pure noise and the coefficients of the remaining library spectra have changed, too. As we can detect, now the minimzed residual spectrum $s - Kx_{opt}$ is no longer white noise but has a distinctive structure and, which is very important, it has some structure on the same wavenumbers as the missing spectrum has spectral lines. Thus it is possible to deduce from the remainder spectrum what kind of spectra we ought to add to the analysis. Because the portion of the missing spectrum has to be explained with the remaining spectra as well as possible, their coefficients are distorted, too, and the error limits are no longer reliable. Thus we must always add new library spectra to the analysis until there is no structure left in the remainder spectrum. If there are different pressure broadenings in s and in the library, it might be helpful to use a couple of library spectra for a single compound. However, a better procedure would be to decrease the resolution so that all lines become sinc-function shaped (see the next chapter).

Figure 4:
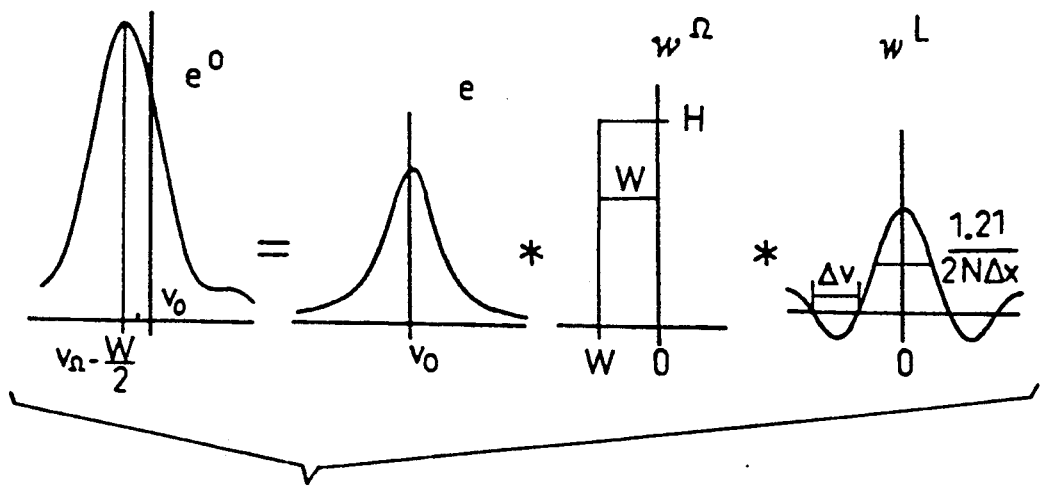
FIG. 4 discloses a situation when the observed line shape $e^0$ is always the convolution of the real line shape e, the boxcar broadening function $w^\Omega$ described in FIG. 3 and the Fourier transform $w^L$ of the boxcar interferogram truncation function.

In FIG. 4 function $w^L$ is a sinc-function, and the interval between its two successive zeroes equals the data interval $\Delta v$ in the spectral domain, which in turn equals $1/(2N\Delta x)$. The FWHH of $w^L$ is approximately the same. The width W of $W^\Omega$ is directly propostional to $v_0$ (the location of the spectral line) and the area of the radiation source. Its height H is inversely proportional to $v_0$ and directly proportional to the surface brightness of the source. In the optimal situation the FWHH's of the three right-hand side curves are approximately equal. The total area of $e^0$ is the product of the areas of e, $w^\Omega$, and $w^L$. The area of $w^L$ is always 1 and can be regarded as dimensionless.

After we have fixed the wavenumber range we want to deal with, the sampling interval in the interferogram is also fixed according to the Nyqvist sampling theorem. However, it still remains to choose the length of the registered interferogram or the amplitude of the mirror movement, which in turn is determined by the used number of the data N. Note that we denote by N the number of the data of the single-sided interferogram. the corresponding number used by the Fast Fourier Transform algorithm is then 2N. We are not going to examine how the number of the data ought to be selected in order to minimize the error limits. As we can see from Eq. 32, the error limits are directly proportional to the standard deviations of the coefficients, which means the square roots of their variances. From Eq. 29 or 33 we get $$\sqrt{Var(x^\epsilon_{opt,j})} = \frac{\sigma_s}{\sqrt{N}} \sqrt{\sum_{l=1}^{M} \frac{(Q_{jl}^{-1})^2}{\|K^{\prime l}\|^2}} \quad (35)$$

Thus the error limits are directly proportional to the standard deviation $\sigma_s$ of the spectral noise and inversely proportional to the square root of the number of the data N. According to the definitions of inner product and norm defined by Eqs. 8 and 5, the remaining square root expression is not an explicit function of N. However, it depends on the shapes of the library spectra.

Let us now examine what happens when we diminish the number of the data N by some factor $1/k$. We see immediately the negative effect that the coefficient $1/\sqrt{N}$ is increased by factor $k^{\frac{1}{2}}$. However, the standard deviation $\sigma_s$ of the noise of the mixture spectrum has changed, too. This change is governed by the Parseval theorem $$\int_{-\infty}^{\infty} n_i^2(x)dx = \int_{-\infty}^{\infty} |n_s(v)|^2 dv, \quad (36)$$

where $n_l$ and $n_s$ are the noise functions in the interferogram and in the spectrum respectively. (These two random processes are a Fourier transform pair.) Becasue the noise $n_l$ is totally white, its "amplitude" is the same everywhere. Thus when the length of the first integral is truncated to one k:th of its original value, the value of the integral is diminished by the same factor $k^{-1}$. So the other integral has to change by same factor. Because we do not change the wavenumber range under investigation, the only possibility is that the "amplitude" of the noise $n_s$, or its standard deviation $\sigma_s$, is diminished by factor $k^{\frac{1}{2}}$. This effect completely cancels the $1/\sqrt{N}$ dependence in Eq. 35.

As we detected above, when reducing the resolution, the coefficient $$\frac{\sigma_s}{\sqrt{N}}$$

on Eq. 35 remains constant. Thus the only possible source of changes in the error limits is the expression $$\sqrt{\sum_{l=1}^{M} (Q_{jl}^{-1})^2 / \|K^{\prime l}\|^2}$$

As mentioned before, the definitions of inner product and norm mean that this expression depends solely on the shapes of the library spectra, when M is fixed. The number of the data itself is not important. All linear changes, where all the library spectra are multiplied by some constant coefficient C, change this square root expression by constant $C^{-1}$. Now the spectra are in practice always computed from the corresponding interferograms by applying the Fast Fourier Transform (FFT) algorithm. A fundamental property of this algorithm is that the data interval in the spectrum is $1/(2N\Delta x)$, where $\Delta x$ is the sampling interval in the interferogram. So when the number of the data is diminished by factor $1/k$, the data interval in the spectral domain is increased by factor k. As far as the data interval ($\approx$ resolution/1,21) stays smaller than the FWHH (full width at half height) of the spectral lines, there exists at least one data at every line and the shape of the spectral lines does not vary considerably. This means that there is only very little use from employing a better resolution than the width of the spectral lines. In the interferogramn domain this means that we can safely truncate the interferogram provided that we do not cut off a considerable portion from the signal.

Let us now define the interferogram truncation function to be a boxcar function having the value of 1 between $X = \mp N\Delta X$ and 0 elsewhere. Because we are only able to register a finite interval of the interferogram, the real, infinitely long interferogram is always multiplied by this function. In the spectral domain this means that the spectra are convolved with the Fourier transform $w^L$ of the truncation function, or $$\Theta^0 = e^\infty * w^L \quad (37)$$

where $$w^L(\nu) = 2N\Delta x \operatorname{sinc}(2N\Delta x \pi \nu), \quad (38)$$

$e^0$ is the mixture spectrum or a library spectrum and $e^\infty$ is the spectrum which would be obtained by transforming the whole interferogram. The FWHH of this sinc-function is approximately $1.21/(2N\Delta x)$, and this is the entity we refer to as the resolution here. As far as N remains larger than $(2\Delta xx\text{FWHH of the spectral lines})^{-1}$, $w^L$ is narrower than the lines of $e^\infty$ and does not have a considerable influence on their shapes. If we still reduce the resolution after this point, the spectral lines suddenly begin to widen and their shapes become determined mainly by $w^L$ instead of their real shapes. This means that the convolution of Eq. 37 then changes the spectra nonlinearly, so that its effect is not a mere multiplication of the square root expression by a constant coefficient. If no apodizaton is applied, the lines begin to resembly sinc-curves. (If apodization is performed, the interferogram noise data are no longer identically distributed and the error analysis is not valid.) Because of the widening, the lines begin to overlap, which makes it harder to discern them from each other. This, in turn, means that the sum expression in Eq. 35 begins to grow. The rate of this growth, however, depends on the amount M of the library spectra used in the analysis and on how near the lines are to each other. For example, if the lines were originally grouped into sets of overlapping lines, the growth rate would not be as fast as it would be were the lines originally situated at approximately equal intervals. Some crude results may be given anyhow. For instance, if we are using a set of at most 50 library spectra, the coefficient of growth of the square root expression normally lies between $k^{\frac{1}{2}}$ and $k^{\frac{1}{2}}$ depending on how the lines are situated. The square root expression also depends on the number of lines in the spectra. This dependence obeys the approximate law that the value of the square root is approximately inversely proportional to the square root of the average number of lines in one spectrum. Thus it can be considered as a constant coefiicient not depending on N.

According to what is said above, the best choice for the resolution would be the FWHH of the spectral lines. So the recorded interferogram should reach from $-1/(2\times\text{FWHH})$ to $1/(2\times\text{FWHH})$. This, however, holds true only if we are unable to adjust the settings of the interferometer. If we can freely set all the parameters of the device, there exist two additional advantages of the resolution reduction. We shall now consider them more closely.

Figure 3:
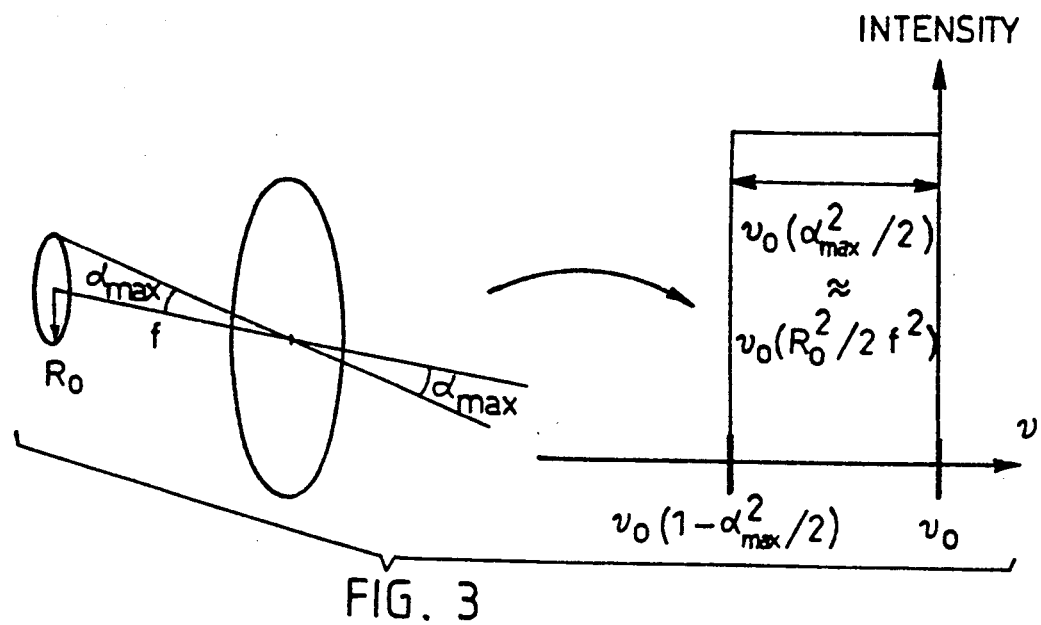
FIG. 3 discloses a situation if the interferometer is properly aligned, but the radiation source is circular instead of an ideal point source, the signal in every individual wavenumber $\nu_0$ is spread uniformly of the interval from $\nu_0(1-\alpha^2/2)$ to $\nu_0$.

As is well known, a non-point radiation source causes all spectral lines to widen. Typically the radiation source (opening) is round, and in that case every monochromatic spectral line is spread out into a boxcar line shape, as is shown in FIG. 3. The width of the box is then directly proportional to the area of the radiation source. This means that the spectrum $e^\infty$ in Eq. 37 is in fact the true spectrum $e$ convolved with the boxcat function $w^\Omega$ arising from the non-zero area of the light source. Thus Eq. 37 can be re-written as $$e^0 = e / w^\Omega * L \quad (39)$$

Because the width of $w^\Omega$ depends on the wavenumber $\nu_0$ of the spectral line under consideration, an exact treatment would require using different $s^\Omega$ for every line. An illustration of Eq. 39 is shown in FIG. 4. Because the FWHH of the convolved line is approximately the sum of the FWHHs of the components of the convolution, the distortions $w^\Omega$ and $w^L$ have a considerable effect only, if their widths are larger than that of the natural widths of the spectral lines. Thus we can safely increase the signal by increasing the radius of the radiation source until the (maximal) width of the boxcar distortion equals the FWHH of the undistorted spectral lines. Correspondingly we can decrease the amount of computation by reducing resolution until the FWHH of the sinc-distortion equals that of the spectral lines. (Which means the optimal truncation of the interferogram.) In case of gaseous specimen, however the natural width of the lines may be so small, that this situation can not be achieved. Anyhow, it is still sensible to make the distortions $w^\Omega$ and $w^L$ of equal kagnitude. Thus we can take this situation as our stating point. Let us now reduce the number of the data by factor $k^{-1}$. As we have stated before, this reduction widens the lines by widening $w^L$ by factor k thus increasing the square root expression of Eq. 35 by a factor of at most $k^{\frac{1}{2}}$, if we use some tens of library spectra. If M is of the order of a couple of hundreds, this factor can be of the order of k. Now, however, we can increase the area of the radiation source by factor k without any considerable further increase in the line widths. Because the area under the spectral liens must then grow by factor k due to the increase of the signal, the only possibility is that the heights of the lines are increased by the same factor k and the change of the spectra is approximately linear. Multiplication of the spectra with constant coefficient k reduces the square root expression by coefficient $k^{-1}$. This is more than enough to cancel the growth of the square root expression in the nonlinear interferogram truncation operation. In practice, however, there may arise difficulties in concentrating the enlarged image of the radiation source on the detector.

The other additional advantage of the resolution reduction is that we are now able to register k interferograms int he same amount of time we previously registered only one single. Because Fourier transforming is a linear operation, co-adding these interferograms means that the corresponding spectra are co-added, too. The errorless spectra e remain the same in every measurement, which means that they become multiplied by k in the summation. This means a simple linear change of the spectra, which in turn means that the square root expression becomes multiplied by $k^{-1}$. The noise of s, on the other hand is different every time, and it does not sum up linearly. From results 25 and 26 we see that teh summed up noise has the distribution $(N(0, k\sigma_g^2)$. Thus the standard deviation $\sigma_g$ of the noise is increased by factor $k^{\frac{1}{2}}$. The total effect is that the error limits become multiplied by factor $k^{\frac{1}{2}}$.

When we finally gather together all the different effects mentioned above, it becomes apparent that if we can freely change all the parameters of the interferometer, as small a resolution should be used as possible. The number of the data N should, however, be at least two or three times as large a the (maximal) number of the library spectra for the structure of the residual spectrum $s - Kx$ to be examinable.

If the library spectra are measured by using a different resolution than in measuring the mixture spectrum, the analysis can fail and large negative coefficients may appear. A similar situation can arise if the line shapes in the library spectra and in the mixture spectrum differ due to nonlinearities or different pressure boradenings. Then some improvement can be achieved by calculating the best non-negative solution instead of the best solution. By non-negative solution we mean such coefficient vector x, which is the solution of the problem 4 subject to the condition that every component of x has to be non-negative. This procedure brings more information into the analysis, because we apply an a priori knowledge of the coefficients. We are now going to derive an algorithm for finding the solution of problem 4 under the non-negativity constraint.

Let us denote d the residual norm $$d(x) = s - Kx$$

Because a norm is always a non-negative quantity, the norm $\|d\|$ has exactly the same minima as its square $\|d\|^2$ so that instead of the norm we can minimize its square. Now $\|d(x)\|^2$ is a convex function of x. This means that for every $x_1$, $x_2$ and $\lambda$, $0 < \|\| < 1$, $$\|d)\lambda x_1 + (1-\lambda)x_2)\|^2 \leq \lambda - d(x_1)\|^2 + (1-\lambda)\|d(x_2)\|^2.$$

This can be seen by using the triangle inequality and the fact that the geometrical mean is always less or equal to the arithmetic mean. The convexity implies that the square norm has only one minimum point, which makes the minimization much simpler.

Especially when other coefficients are held fixed and only one coefficient $x_j$ is varied, $\|d\|^2$ is a convex function of one variable. Thus at the optimum point $x_{opt}$ there exist two possibilities. Either $$\frac{\partial \|d(x_{opt})\|^2}{\partial x_j} = 0$$

(where all the components except the j:th are fixed to $x_{opt}$) or, if the zero of the derivatives does not lie in the allowed area $x_j \geq 0$, $$x_{opt,j} = 0,$$

which means that $x_{opt,j}$ is on the border between the allowed and the forbidden areas. This can be proved as follows:

1) If the zero of $\partial \|d(x_{opt})\|^2 / \partial x_j$ lies in the allowed area $x \geq 0$, $x_{opt,j}$ clearly has to equal this zero.

2) If the zero of $\partial \|d(x_{opt})\|^2 / \partial x_j$ lies in the forbidden area $x_j < 0$, the derivative is positive, when $s_j \leq 0$, because of the convexity of $\|d(x)\|^2$. Thus, if $x_{opt,j} > 0$, diminishing of $x_{opt,j}$ would diminish the value of $\|d\|^2$ without exiting the allowed area. Thus the only possibility is that $x_{opt,j} = 0$.

We are not able to state the following condition for optimality:

At the unique solution point $x_{opt}$ of the minimization problem 4 with non-negative components of x either of the following conditions holds for each component $x_j$:

$$\left( \frac{\partial \|d(x_{opt})\|^2}{\partial x_j} = 0 \text{ and } x_j \leq 0 \right) \quad (40)$$

or $$\left( x_j = 0 \text{ and } \frac{\sigma \|d(x_{opt})\|^2}{\sigma x_j} > 0 \right).$$

Figure 5:
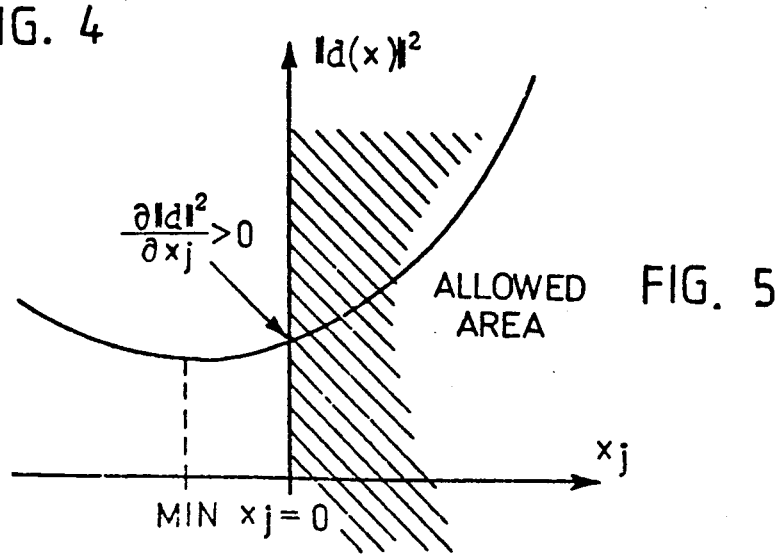
FIG. 5 discloses a situation when for every component $x_j$ of the optimal non-negative coefficient vector $x_{opt}$ either one of the following conditions holds.

This is illustrated in FIG. 5. The so-called Kuhn-Tucker criteria (see some textbook of optimization, e.g., [3]), which in case of a convex object function are a necessary and a sufficient condition for optimality, would give quite the same condition.

The partial derivatives are very simple to calculate, and we obtain $$\nabla_x(\|d(x)\|^2) = 2(Ax - y), \quad (41)$$

where A is the inner product matrix defined in Eq. 10 and y is given by Eq. 11. The individual partial derivatives are the components of this gradient, or $$\frac{\partial(\|d\|^2)}{\partial x_j} = (\nabla_x \|d(x)\|^2)_j = 2\left( \sum_{i=1}^{M} A_{ij} x_i - y_j \right). \quad (42)$$

If we include some background spectra in the used set of library spectra, it is sensible not of impose the non-negativity constraint on their coeffieicnts. The background spectra consist of all the compounds, which are present also when measuring the background (such as water and carbon dioxide), plus a constant function and simple cosine curves, which can be generated by some erroneous data in the interferogram. When this is taken into account, too, the minimum point can be found e.g. by the following algorithm:

1) Choose some starting point $x = x_0$, for instance $x_0 = (0, 0, \ldots, 0)^T$ or $x_0 = A^{-1}y$. Insert $j = 1$.

2) Calculate $$x_j = \frac{y_j - \Sigma_{i \neq j} A_{ji} x_i}{A_{jj}},$$

which according to Eq. 42 is the zero point of $\partial \|d(x\|^2 / \partial x_j$. If $x_j < 0$ and the coefficient $j$ has the non-negativity constraint, re-insert $x_j = 0$. Insert $j = j + 1$.

3) If $j \leq M$ (where M is the amount of library spectra used in the analysis), return to step 2). Otherwise continue form step 4).

4) Calculate $$G = \frac{1}{2} \nabla_x (\|d(x)\|^2) = Ax - y.$$

If for every component $G_j$ of G either $|G_j| < \epsilon_1$ or ($G_j > 0$ and $x_j < \epsilon_2$), where $\epsilon_1$ and $\epsilon_2$ are suitable small real numbers, stop. Otherwise, insert $j = 1$ and return to step 2).

What we claim is:

1. A procedure for analyzing a multicomponent FT-IR spectrum of an unknown mixture of gases, the procedure comprising the steps of:

providing a gas spectrum analyzer in which a set of FT-IR library spectra of pure molecular gases, measured in known pressures, are stored as vectors k having N components and by which analyzer inner products for all possible combinations of two vectors k are calculated and stored;

measuring an FT-IR spectrum s for the unknown mixture of gases;

storing by said gas spectrum analyzer the FT-IR spectrum s as a vector having N components;

selecting from said set of stored FT-IR library spectra of pure molecular gases those M gases which are expected to be contained in the unknown mixture of gases;

forming from the library vectors k of the selected M gases a basis matrix K;

forming an orthogonal basis matrix K' by deforming the vectors k chosen for the matrix K to orthogonal vectors k' so that inner products of these vectors k' with each other but not with themselves are zero;

calculating and storing the inner products of said orthogonal vectors k' with themselves;

forming and storing a basis transformation matrix Q so that K=K'Q;

forming and storing an inverse matrix $Q^{-1}$ of the matrix Q;

calculating an optimal coefficient vector x' for the spectrum s of the unknown mixture of gases in the orthogonal basis by using for its components $x_j'$ the equation $$x_j' = \frac{(k'^j|s)}{(k'^j|k'^j)} \ ;$$

calculating a coefficient vector x so that $x=Q^{-1} X'$;

calculating partial pressures of the pure gases in the unknown mixture of gases by multiplying the measuring pressures of the selected library spectra by their coefficients $x_j$ thus forming an analysis result for the unknown mixture of gases in the form of the partial pressures of those pure molecular gases expected to be contained in said unknown mixture of gases; and comparing the vector representing the measured spectrum s to its analysis result in order to evaluate the analysis result and thus the successfulness of selection of the pure molecular gases expected to be contained in said unknown mixture of gases.

2. A procedure according to claim 1 wherein comparison of the measured spectrum s to its analysis result reveals mismatch the procedure further comprising the steps of selecting a new pure molecular gas to be added to the gases expected to be contained in the unknown mixture of gases;

adding the library vector $k^{M-1}$ of the new selected pure molecular gas to the basis matrix K by:

calculating a new orthogonal vector $k'^{m+1}$ so that its inner product with the other orthogonal vectors k' but not with itself are zero;

calculating and storing an inner product of the new orthogonal vector $k'^{M+1}$ with itself;

adding a new column to the transformation matrix Q and storing this new matrix;

forming and storing a new inverse matrix $Q^{-1}$ on the basis of the new matrix Q by adding a new column to the inverse matrix $Q^{-1}$;

calculating anew component $x'_{m+1}$ for the orthogonal coefficient vector x' of the spectrum s to be analyzed by the equation $$x_{M+1}' = \frac{<k'^{M+1}|s>}{<k'^{M+1}|k'^{M+1}>}$$

and adding it to the vector x'; and calculating a new coefficient vector x so that $x=Q^{-1}x'$.

3. A procedure according to claim 1 further comprising the steps of:

evaluating a deviation $\sigma_s$ for the noise of the spectrum s;

calculating variances for the coefficients $x_j$ of the vector x by using the equation $$Var(x_j) = \frac{\sigma_s^2}{N} \sum_{l=1}^{M} \frac{(Q_{jl}^{-1})^2}{<k'^l|k'^l>}$$

and calculating error limits $v_j(p)$ for the coefficients $x_j$ by the equation $$v_j = \sqrt{Var(x_j)} \ \Phi^{-1}\left(\frac{1+p}{2}\right)$$

which p is the probability by which the error for the library spectrum j if between the limits $(-v_j, v_j)$ and $\Phi^{-1}$ is the inverse of the distribution function of the one-dimensional standardized normal distribution.

4. A procedure according to claim 2 further comprising the steps of:

evaluating a deviation $\sigma_s$ for the noise of the spectrum s;

calculating variances for the coefficients $x_j$ of the vector x by using the equation $$Var(x_j) = \frac{\sigma^2}{N} \sum_{i=1}^{M} \frac{(Q_n^{-1})^2}{<k'^l|k'^l>}$$

and calculating error limits $v_j(p)$ for the coefficients $x_j$ by the equation $$v_j = \sqrt{Var(x_j)} \ \Phi^{-1}\left(\frac{1+p}{2}\right)$$

in which p is the probability by which the error for the library spectrum j is between the limits $(-v_j, v_j)$ and $\Phi^{-1}$ is the inverse of the distribution function of the one-dimensional standardized normal distribution.

5. A procedure according to claim 2 further comprising the steps of:

calculating a variance for the new coefficient x by the equation $$Var(x_{M+1}) = \frac{\sigma^2}{N<k'^{M+1}|k'^{M+1}>} \ ;$$

calculating values to be added to the variances of the coefficients $x_j$, $j=1, \ldots, M$ by the equation $$\frac{\sigma^2}{N} \cdot \frac{(Q_{M+1}^{-1})^2}{<k'^{M+1}|k'^{M+1}>} \ ;$$

adding said values to the variances of the coefficients $x_j$, $j=1, \ldots, M$; and calculating new error limits $v_j(p)$ for the coefficients $x_j$ by the equation $$v_j = \sqrt{Var(x_j)} \ \Phi^{-1}\left(\frac{1+p}{2}\right)$$

in which p is the probability by which the error for the library spectrum j is between the limits $(-v_j, v_j)$ and $\Phi^{-1}$ is the inverse of the distribution function of the one-dimensional standardized normal distribution.

* * * * *

UNITED STATES PATENT AND TRADEMARK OFFICE
CERTIFICATE OF CORRECTION

PATENT NO. : 5,313,406

DATED : May 17, 1994

INVENTOR(S) : Kauppinen, et al.

It is certified that error appears in the above-identified patent and that said Letters Patent is hereby corrected as shown below:

Column 1, line 16, "unknonw" should be --unknown--.

Column 1, line 17, "co not inow" should be --do not know--.

Column 1, line 19, "f" should be --of--.

Column 1, line 20, "wih" should be --with--.

Column 1, line 22, "patial" should be --partial--.

Column 1, line 25, "spcectra" should be --spectra--.

Column 1, line 37, "m" should be --M--.

Column 1, line 41, "possible" should be --possibly--.

Column 1, line 52, "ar" should be --are--.

Column 1, line 58, "treeated" should be --treated--.

Column 2, line 33, "unexpalined" should be --explained--.

Column 2, line 38, "comonents" should be --components--.

Column 2, line 48, "fector" should be --vector--.

Column 2, line 50, "norm" should be --norms--.

Column 2, line 52, "solutio" should be --solution--.

Column 2, line 56, "$V|s\text{-}Ks|=0$" should be --$\nabla_x \| s - Kx \| = 0$--.

Column 2, line 62, "nkown" should be --known--.

Column 2, line 66, "square" should be --squares--.

Column 2, line 67, "$K^3$" should be --$K^j$--.

Column 3, line 1, "meeded" should be --needed--.

UNITED STATES PATENT AND TRADEMARK OFFICE
CERTIFICATE OF CORRECTION

PATENT NO. : 5,313,406

DATED : May 17, 1994

INVENTOR(S) : Kauppinen, et al.

It is certified that error appears in the above-identified patent and that said Letters Patent is hereby corrected as shown below:

Column 3, line 3, "theinner produce" should be --the inner product--.

Column 3, line 4, "dn" should be --and--.

Column 3, line 12, "Likwaise" should be --Likewise--.

Column 3, line 20, formula (10), superscript "1" should be superscript --i--.

Column 3, line 27, "lirary specra" should be --library spectra--.

Column 3, line 36, "(see e.q. '2 p. 179])" should be --(see e.g. [2, p. 179])--.

Column 3, line 46, "libray" should be --library--.

Column 4, line 5 (second equation of formula 12), " $K'^2 = K^2 - \frac{(K^2|K'^1)}{\|K'^1\|^2}$ " should be -- $K'^2 = K^2 - \frac{(K^2|K'^1)}{\|K'^1\|^2} K'^1$ --.

Column 4, lines 11 and 12 (third equation of formula 12) " $K'^j = K^j - \sum_{x=1}^{j-1} \frac{<K^j|K'^x>}{\|K'^x\|^2}$ " should be -- $K'^j = K^j - \sum_{r=1}^{j-1} \frac{(K^j|K'^r)}{\|K'^r\|^2} K'^r$ --.

Column 4, line 30 (third equation of formula 13), " $K^j = \sum_{x=1}^{j-1} \frac{<K^j|K'^x>}{\|K'^x\|^2} K'^x + K'^j$ " should be -- $K^j = \sum_{r=1}^{j-1} \frac{(K^j|K'^r)}{\|K'^r\|^2} K'^r + K'^j$ --.

Column 5, line 3, " $<K'^i|K'^j> = \delta_{ij}$ " should be -- $\langle K'^i | K'^j \rangle = \delta_{ij}$ --.

Column 5, line 21, delete "5" under the word "or".

Column 5, line 23, "'opt,j'" should be --$^x$opt,j--.

Column 5, line 43, "S°", second occurrence, should be --$S^c$--.

Column 5, lines 48, 51 and 59, "$X_{opt}{}^0$" should be --$x^0_{opt}$--.

Column 5, line 49 and 62, "$x_{opt}{}^c$" should be --$x^c_{opt}$--.

UNITED STATES PATENT AND TRADEMARK OFFICE
CERTIFICATE OF CORRECTION

PATENT NO. : 5,313,406

DATED : May 17, 1994

INVENTOR(S) : Kauppinen, et al.

It is certified that error appears in the above-identified patent and that said Letters Patent is hereby corrected as shown below:

Column 5, line 55, "$s_{opt}^e$" should be --$x^e_{opt}$--.

Column 5, line 59, the end of equation 23b, "$'A'^1y'^0$" should be --$^1A'^{-1}y'^0$--.

Column 6, line 3, "alsways" should be --always--.

Column 6, line 19, "Let $z_1 \div N(\mu_{1,1}^2)$ be independent and $a_1$ g R." should be --Let $z_i \div N(\mu_i, \sigma_i^2)$ be independent and $a_i \varepsilon$ R--.

Column 6, line 23, at the end of formula 26, subscript "1" should be subscript --i--, in
    both occurrences.

Column 6, line 30, "$x_{opt}^e$" should be --$x^e_{opt}$--.

Column 6, line 55, " $E(y'_j{}'y'_k{}^e)$ " should be -- $E(y'^e_j y'^e_k)$ --.

Column 6, line 56, insert --Now--.

Column 6, line 58, " $E(y'_i{}^e y'_i{}^e)$ " should be -- $E(y'^e_j y'^e_k)$ --.

Column 7, line 6, "$s'^3_{opt}$" should be --$x'^e_{opt}$--.

Column 7, lines 36 and 37, " $[x_{opt,j}{}^0 - v_j, s_{opt,j}{}^0 v_j]$ " should be -- $[x^0_{opt,j} - v_j, x^0_{opt,j} + v_j]$ --.

Column 7, line 39, " $P(x_{opt,j}{}^e \varepsilon [-v_j, v_j]) = p$ " should be -- $P(x^e_{opt,j} \varepsilon [-v_j, v_j]) = p$ --.

Column 7, lines 44, 47, 52, 58 and 65, insert a comma (,) between "opt" and "j".

Column 8, lines 4, 12 and 19, insert a comma (,) between "opt" and "j".

Column 8, line 44, "$Q_{M+1j}$, j 22M + 1" should be --$Q_{M+1,j}$ j > M + 1--.

Column 9, lines 1 and 2, "Var($s_{opt,M}+1^e$)" should be --Var($x^e_{opt,M+1}$)--.

Column 9, line 3, "Var($x_{opt,j}^e$)" should be --Var($x^e_{opt,j}$)--.

UNITED STATES PATENT AND TRADEMARK OFFICE
CERTIFICATE OF CORRECTION

PATENT NO. : 5,313,406
DATED : May 17, 1994
INVENTOR(S) : Kauppinen, et al.

It is certified that error appears in the above-indentified patent and that said Letters Patent is hereby corrected as shown below:

Column 9, line 31, insert subscript "max" between "a$^2$" and "/2".

Column 10, line 24, "not" should be --now--.

Column 11, line 28, "isinversely" should be --is inversely--.

Column 12, line 19, "k½" should be --k$^{-½}$--.

Column 13, line 42, "coefiicient" should be --coefficient--.

Column 13, line 59, "boxcat" should be --boxcar--.

Column 13, line 63, equation 39, "e$^0$=eIw$\Omega$*L" should be --e$^0$=e*w$\Omega$*L--.

Column 13, line 67, "s$^\Omega$" should be --w$^\Omega$--.

Column 14, line 41, "int he" should be --in the--.

Column 14, line 51, "teh" should be --the--.

Column 14, line 52, "(O,k$\sigma_g^2$)" should be --(O,k$\sigma^2_s$)--.

Column 14, line 53, "$\sigma_g$" should be --$\sigma_s$--.

Column 14, line 55, "k½" should be --k$^{-½}$--.

Column 14, line 61, "a" should be --as--.

Column 15, line 1, "boradenings" should be --broadenings--.

Column 15, line 20, "$x_1$, $x_2$ and $\lambda$, 0<| |<1" should be --$x_1$, $x_2$ and $\lambda$, 0<$\lambda$<1--.

Column 15, line 22, in the middle of the equation, "$\|^{2\le\lambda-}$d" should be --$\|^2 \le \lambda \|$d--.

Column 15, line 49, "$s_j \le 0$" should be --$x_j \ge 0$--.

Column 15, line 58, "$x_i$" should be --$x_j$--.

Column 15, lines 66 and 67, in both the top and the bottom of the equation, "$\sigma$" should be --$\partial$--.

UNITED STATES PATENT AND TRADEMARK OFFICE
CERTIFICATE OF CORRECTION

PATENT NO. : 5,313,406

DATED : May 17, 1994

INVENTOR(S) : Kauppinen, et al.

It is certified that error appears in the above-identified patent and that said Letters Patent is hereby corrected as shown below:

Column 17, line 22 (claim 1), "X'" should be --x'--.

Column 17, line 38 (claim 1), after "steps of" insert --:--.

Column 17, line 42 (claim 2), "$k^{M-1}$" should be --$k^{M+1}$"

Column 17, line 44 (claim 2), "$k^{\overline{m}+1}$" should be --$k^{M+1}$--.

Column 17, line 54 (claim 2), "$x'_{m+1}$" should be --$x'_{M+1}$--.

Column 17, line 60 (claim 2), delete the "prime symbol (')" after the number "1".

Column 18, line 15 (claim 3), before "which p", insert --in--.

Column 18, line 16 (claim 3), "if" should be --is--.

Column 18, lines 27 and 28, " $Var(x_j) = \frac{\sigma^2}{N} \sum_{i=1}^{M} \frac{(Q_n^{-1})^2}{<k^1|k^1>}$ " should be -- $Var(x_j) = \frac{\sigma_s^2}{N} \sum_{i=1}^{M} \frac{(Q_{ji}^{-1})^2}{\langle k^{-1}|k^{-1}\rangle}$ --.

Column 18, line 45, "$\sigma^2$" should be --$\sigma_s^2$--.

Column 18, line 52 (claim 5), "$(Q^{-1}_{M+1})^2$" should be --$(Q^{-1}_{j,M+1})^2$--.

Column 2, line 52, "effeict" should read --effect--.

Signed and Sealed this

Sixteenth Day of January, 1996

Attest:

*Attesting Officer*

BRUCE LEHMAN

*Commissioner of Patents and Trademarks*